United States Patent
Ahlers et al.

(10) Patent No.: US 9,504,978 B2
(45) Date of Patent: Nov. 29, 2016

(54) COOLED REACTOR FOR THE PRODUCTION OF DIMETHYL ETHER FROM METHANOL

(71) Applicants: Bernd Ahlers, Dietzenbach (DE); Manuela Gil De Tober, Medellin (CO); Eckhard Seidel, Frankfurt am Main (DE)

(72) Inventors: Bernd Ahlers, Dietzenbach (DE); Manuela Gil De Tober, Medellin (CO); Eckhard Seidel, Frankfurt am Main (DE)

(73) Assignees: L'AIR LIQUIDE, SOCIÉTÉ ANONYME POUR L'ETUDE ET L'EXPLOITATION DES PROCÉDÉS GEORGES CLAUDE, Paris (FR); AIR LIQUIDE GLOBAL E&C SOLUTIONS GERMANY GMBH, Frankfurt am Main (DE)

( * ) Notice: Subject to any disclaimer, the term of this patent is extended or adjusted under 35 U.S.C. 154(b) by 52 days.

(21) Appl. No.: 14/346,370

(22) PCT Filed: Sep. 18, 2012

(86) PCT No.: PCT/EP2012/068324
§ 371 (c)(1),
(2) Date: Mar. 21, 2014

(87) PCT Pub. No.: WO2013/041516
PCT Pub. Date: Mar. 28, 2013

(65) Prior Publication Data
US 2015/0038745 A1 Feb. 5, 2015

(30) Foreign Application Priority Data
Sep. 23, 2011 (DE) .................. 10 2011 114 228

(51) Int. Cl.
*C07C 43/00* (2006.01)
*B01J 8/02* (2006.01)
*B01J 8/04* (2006.01)
*B01J 8/06* (2006.01)
*C07C 41/09* (2006.01)

(52) U.S. Cl.
CPC ............ *B01J 8/02* (2013.01); *B01J 8/0453* (2013.01); *B01J 8/0492* (2013.01); *B01J 8/0496* (2013.01); *B01J 8/067* (2013.01); *C07C 41/09* (2013.01); *B01J 2208/00274* (2013.01); *B01J 2208/00362* (2013.01); *B01J 2208/00371* (2013.01); *B01J 2208/024* (2013.01); *C07C 2101/16* (2013.01)

(58) Field of Classification Search
CPC ... C07C 41/09; C07C 43/04; C07C 2101/16; B01J 2208/00274; B01J 2208/00362; B01J 2208/00371; B01J 2208/024; B01J 8/02; B01J 8/0453; B01J 8/0492; B01J 8/0496; B01J 8/067; A61K 31/4745; A61K 31/498; A61K 31/519; A61K 9/0056; A61K 9/0058; A61K 9/006; A61K 9/2009
See application file for complete search history.

(56) References Cited

U.S. PATENT DOCUMENTS

| | | | |
|---|---|---|---|
| 2,014,408 A | 9/1935 | Woodhouse et al. | |
| 4,058,576 A | 11/1977 | Chang et al. | |
| 4,366,327 A | 12/1982 | Convers et al. | |
| 4,542,252 A | 9/1985 | Graziani et al. | |
| 2009/0023958 A1 | 1/2009 | Jun et al. | |
| 2011/0065963 A1 | 3/2011 | Guo et al. | |
| 2012/0142973 A1 | 6/2012 | Su et al. | |

FOREIGN PATENT DOCUMENTS

| | | | |
|---|---|---|---|
| CN | 2900523 | * | 5/2006 |
| CN | 2900523 | * | 5/2007 |
| CN | 2900523 Y | | 5/2007 |
| CN | 101768054 A | | 7/2010 |
| CN | 101903323 | * | 12/2010 |
| CN | 101903323 A | | 12/2010 |
| DE | 3115496 A1 | | 1/1982 |
| DE | 3817816 A1 | | 11/1989 |
| EP | 2213367 A1 | | 8/2010 |
| WO | WO 2011095270 A1 | | 8/2011 |

OTHER PUBLICATIONS 523 translated 2007.*
523 2006.*
323 2010.*
Farsi, et al., "Modeling and Optimization of MeOH to DME in Isothermal Fixed-bed Reactor", International Journal of Chemical Reactor Engineering, vol. 8, Article A79, Dec. 2010, pp. 1-14.
Hoever, "Dimethyl Ether", Ullmann's Encyclopedia of Industrial Chemistry, Sixth Edition, Electronic Release, Dec. 1998, pp. 1-6.

* cited by examiner

*Primary Examiner* — Yevegeny Valenrod
*Assistant Examiner* — Blaine G Doletski
(74) *Attorney, Agent, or Firm* — Leydig, Voit & Mayer, Ltd.

(57) ABSTRACT

A cooled reactor for the production of dimethyl ether by catalytic dehydration of methanol in the gas phase, the reactor having an adiabatic catalyst bed as starting zone, a moderator zone cooled by direct or indirect heat exchange, and optionally an adiabatic catalyst bed as conditioning zone. The conversion of methanol to dimethyl ether is increased and the formation of undesired by-products is decreased.

20 Claims, 5 Drawing Sheets

PRIOR ART

COOLED REACTOR FOR THE PRODUCTION OF DIMETHYL ETHER FROM METHANOL

CROSS-REFERENCE TO RELATED APPLICATIONS

This application is a U.S. National Phase application under 35 U.S.C. §371 of International Application No. PCT/EP2012/068324, filed on Sep. 18, 2012, and claims benefit to German Patent Application No. DE 10 2011 114 228.6 filed on Sep. 23, 2011. The International application was published in English on Mar. 28, 2013, as WO 2013/041516 A2 under PCT Article 21(2).

FIELD

This invention relates to a cooled reactor for the production of dimethyl ether (DME) by acid-catalyzed dehydration of methanol in the gas phase on solid catalysts, in particular on the basis of alumina, which allows an optimized reaction control for a high yield of the target product as well as the minimization of the formation of by-products. The invention furthermore relates to a process for the DME production with the reactor according to the invention.

BACKGROUND

The catalytic production of dimethyl ether (DME) from methanol by catalytic dehydration has been known for many years. The U.S. Pat. No. 2,014,408 for example describes a process for the production of DME from methanol on catalysts such as aluminum oxide, titanium oxide and barium oxide, with temperatures of 350 to 400° C. being preferred.

Further information on the prior art and on the current practice of the production of dimethyl ether can be found in Ullmann's Encyclopedia of Industrial Chemistry, Sixth Edition, 1998 Electronic Release, keyword "dimethyl ether". In Chapter 3 "Production" it is explained in particular that the catalytic conversion of pure, gaseous methanol is performed in a fixed-bed reactor.

From the point of view of reaction engineering, fixed-bed reactors preferably are used for the catalytic dehydration of methanol to DME in the gas phase, since they are characterized by constructive simplicity. The German laid-open publication DE 3817816 describes a process integrated in a methanol synthesis plant for producing dimethyl ether by catalytic dehydration of methanol without previous separation of the synthesis gas not converted in the methanol reactor. As dehydration reactor a simple fixed-bed reactor is used. When the same is designed for temperature control without any additional measures, but is merely surrounded with an outer insulation to avoid heat losses, it is also referred to as adiabatic fixed-bed reactor.

The dehydration of methanol to dimethyl ether according to the reaction equation

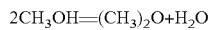

$$2CH_3OH = (CH_3)_2O + H_2O$$

is an exothermal equilibrium reaction; hence it follows that from a thermodynamic point of view high degrees of conversion are achieved at reaction temperatures as low as possible. On the other hand, from a reaction-kinetic point of view a minimum reaction temperature is required, in order to ensure sufficient reaction rates and thus acceptable methanol conversions. What is disadvantageous in the adiabatic fixed-bed reactors used so far is the missing possibility of ensuring an optimum temperature control, to ensure high degrees of conversion and to minimize the formation of by-products.

The formation of by-products, such as carbon monoxide CO, carbon dioxide $CO_2$, hydrogen $H_2$ and methane $CH_4$, preferably is effected at higher temperatures. As a possible cause for the formation of the three first-mentioned by-products, the steam cracking of methanol in the feed stream or of already formed DME with steam is assumed, which steam is formed as reaction by-product. Methane for example can be formed as a consecutive reaction of the formed carbon oxides with hydrogen. The formation of these by-products is undesirable, since they impair the purity of the reaction product and reduce the selectivity of the reaction to DME.

The theoretical study "Modeling and Optimization of MeOH to DME Isothermal Fixed-bed Reactor", Farsi et al., International Journal of Chemical Reactor Engineering, Volume 8, 2010, Article A79, describes the optimum temperature profile of the reactor temperature for the catalytic dehydration of methanol to dimethyl ether in a quasi (or largely) isothermal fixed-bed reactor, in which the solid catalyst is arranged in tubes which on the shell side are surrounded by partly evaporating water as cooling medium. By using a genetic algorithm which takes account of the thermodynamic and kinetic aspects of the dehydration reaction, a temperature profile exponentially decreasing from the reactor inlet to the reactor outlet is calculated as optimum, wherein the reactor inlet temperature is about 800 K and the reactor outlet temperature is about 560 K. Proceeding from this axial temperature profile, a methanol conversion of about 86% is calculated for the optimized isothermal reactor, whereas it is merely about 82% in the adiabatic reactor. However, said paper does not provide any information as to how an optimized fixed-bed reactor should constructively be designed for the production of DME from methanol. Moreover, merely the methanol conversion, but not the formation of possible by-products is used as criterion for optimization.

SUMMARY

An aspect of the invention provides a reactor, comprising: an adiabatic region; a cooled region; a fixed bed zone; a starting zone; and moderator zone, wherein the reactor is configured to produce dimethyl ether (DME) by heterogeneously catalyzed dehydration of a gaseous feed stream comprising methanol, wherein the dehydration occurs over a solid catalyst suitable to dehydrate methanol to DME under dehydration conditions, (a) wherein the reactor is configured such that, in the starting zone, after entry into the reactor, the gaseous feed stream initially flows through the adiabatic region, comprising the catalyst, wherein, in the starting zone, a first part of the methanol comprised in the feed stream exothermally reacts to provide DME under methanol dehydration conditions, wherein, in starting zone, a feed stream temperature is increased with respect to a reactor inlet temperature, and the feed stream temperature does not exceed a fixed maximum temperature, (b) wherein the reactor is configured such that, in the moderator zone, the gaseous feed stream subsequently passes through at least one cooled region, wherein, in the moderator zone, reaction heat released is at least partly dissipated and the feed stream temperature increase is at least reduced, (c) wherein the reactor is configured such that, before the gaseous feed stream exits the reactor, the gaseous feed stream optionally flows through a last adiabatic region, comprising the catalyst, in the form of a conditioning zone, wherein, in the conditioning zone, a second part of the methanol comprised in the feed stream exothermally reacts to provide DME under methanol dehydration conditions, and the feed stream temperature is increased to a reactor outlet temperature.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
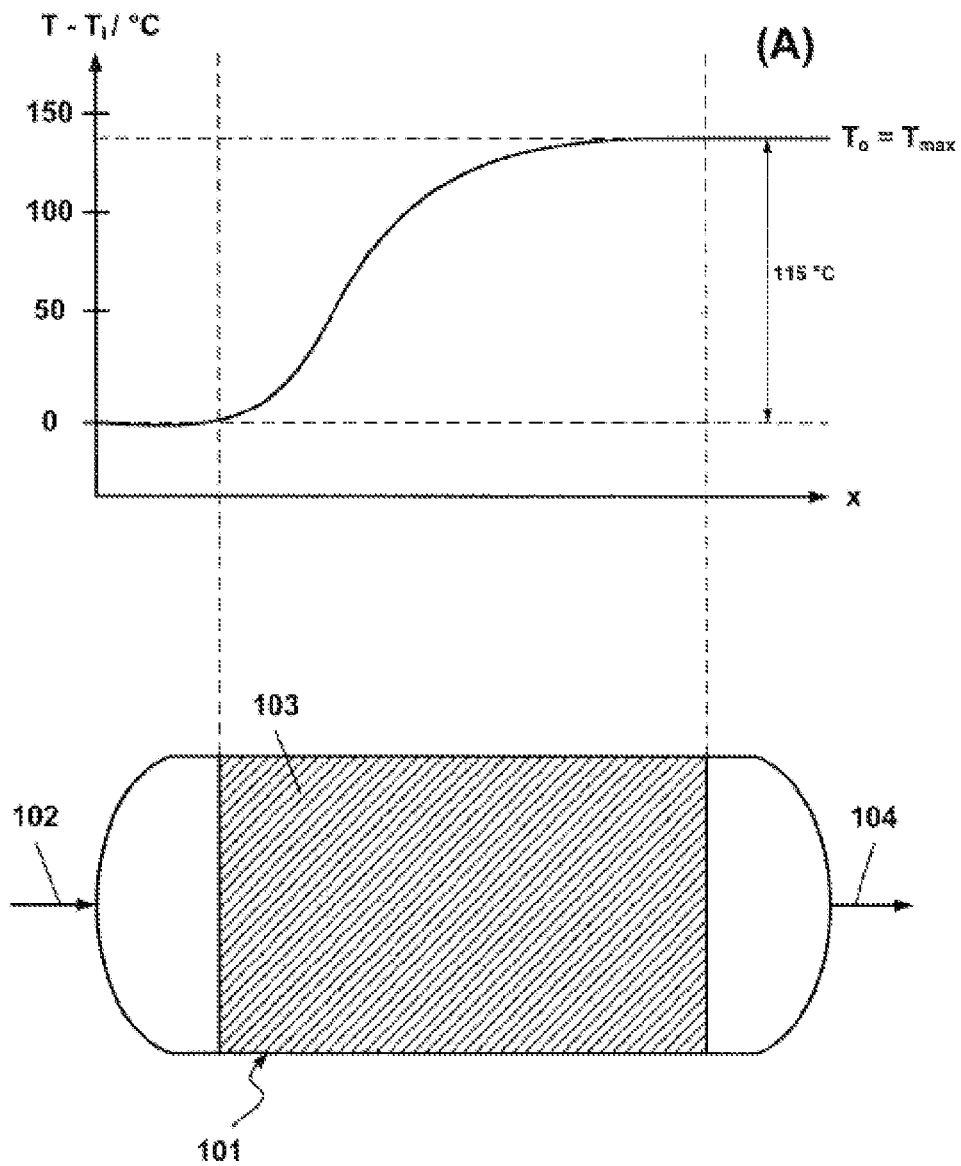
FIG. 1 schematically shows an adiabatic fixed-bed reactor according to the prior art (comparative example)

An aspect of the present invention provides a reactor for the production of dimethyl ether by acid-catalyzed dehydration of methanol in the gas phase, which allows an optimized reaction control with regard to a high yield of the target product and the minimization of the formation of by-products.

An aspect of the invention provides a reactor for the production of dimethyl ether (DME) by heterogeneously catalyzed dehydration of a gaseous or vaporous feed stream containing methanol on a solid catalyst active for the dehydration of methanol to DME, wherein the catalyst is present in at least one fixed-bed zone in the reactor, which is characterized in that (a) the reactor includes at least one adiabatic and at least one cooled region, (b) after entry into the reactor, the gaseous or vaporous feed stream initially flows through an adiabatic region filled with catalyst (starting zone), wherein in the starting zone a first part of the methanol contained in the feed stream exothermally reacts to obtain DME under dehydration conditions, and wherein the temperature of the feed stream is increased with respect to the reactor inlet temperature, wherein a fixed maximum temperature is not exceeded, (c) the gaseous or vaporous feed stream subsequently passes through at least one cooled region (moderator zone) and optionally further adiabatic regions with catalyst filling and/or cooled regions, wherein in the moderator zone the reaction heat released is at least partly dissipated and the increase in temperature of the feed stream is reduced or reversed, (d) before its exit from the reactor, the gaseous or vaporous feed stream optionally flows through a last adiabatic region filled with catalyst (conditioning zone), wherein in the conditioning zone a further part of the methanol contained in the feed stream exothermally reacts to obtain DME under dehydration conditions, and wherein the temperature of the feed stream is increased to the reactor outlet temperature.

An aspect of the invention also relates to a process for the production of dimethyl ether (DME) by heterogeneously catalyzed dehydration of a gaseous or vaporous feed stream containing methanol on a solid catalyst active for the dehydration of methanol to DME, which comprises the following steps:

(a) providing a gaseous or vaporous feed stream containing methanol, (b) catalytic conversion of the feed stream containing methanol under dehydration conditions to obtain a product stream containing DME, (c) recovering the DME from the product stream containing DME, wherein the process according to the invention is characterized in that the catalytic conversion in step (b) is effected in an inventive reactor.

The reactor according to the invention is based on the idea that the adiabatic heating by the reaction heat released in the starting zone initially increases the reaction rate to technically acceptable values. In this way, part of the energy required for superheating the feed stream is saved. The minimum reactor inlet temperature should, however, lie above the light-off temperature for the present feed mixture, which can be determined by routine experiments.

To avoid too high gas temperatures, which would prove troublesome due to a shift of the reaction equilibrium back to the educt side and the formation of undesired by-products, the gaseous feed stream which still contains a large amount of non-converted methanol enters into the moderator zone succeeding the starting zone in flow direction. In said moderator zone, the increase in temperature is decelerated or reversed by means of the cooling effected by direct or indirect heat exchange. Cooling, however, only is expedient from a temperature increase of about 30° C. above the feed temperature or at partial methanol conversions greater than 20%, as otherwise the range of acceptable reaction rates is left.

The optimum operating temperatures are dependent on the composition of the feed mixture. The temperature profile in the reactor is set such that the optimum temperatures belonging to the feed mixture and to the reactor inlet temperature are not exceeded or not reached at any time. These temperatures lie in a range of 30 to 90° C. above the feed temperature. This avoids the undesired formation of by-products, such as for example CO, $CO_2$, $CH_4$ and $H_2$. In the moderator zone, the mean reactor temperature should rather lie in the upper part of the above-mentioned optimum temperature range, so that high reaction rates are achieved and the catalyst is optimally utilized.

The mode of operation of the reactor according to the invention is independent of the type of solid catalyst used, as long as the catalyst is active for the dehydration of methanol to DME. The chosen type of catalyst, however, possibly influences the reaction conditions, such as the reactor inlet temperature or kick-off temperature of the dehydration reaction and the admissible maximum temperature with regard to a possible thermal damage of the catalyst, but also with regard to the occurrence of side reactions, and the space velocity to be adjusted. Preferably, alumina-based acidic catalysts are used, as they are available for example from Süd-Chemie AG, Munich. Usual space velocities for the catalytic dehydration of methanol to DME in the gas phase lie between 0.1 and 10 kg/(kg h), usual reactor pressures lie between 1 and 30 bar (abs.), but in part can also assume higher values. Suitable reaction temperatures lie between 200 and 500° C., preferably between 250 and 400° C.

It was found to be particularly favorable that the desired reactor outlet temperature is approached asymptotically, as in this case the catalyst is optimally utilized by approaching the reaction equilibrium for the respective reaction conditions. For configurations of the reactor according to the invention in which the desired reactor outlet temperature is not approached asymptotically, it is advantageous when a conditioning zone is provided downstream of the moderator zone. Said conditioning zone in turn consists of an adiabatic catalyst bed in which a last part of the methanol contained in the feed stream reacts exothermally to obtain DME. The gas temperature is increased to the desired reactor outlet temperature, and in the stationary state of the reactor operation it is either equal to the maximum temperature, but preferably less than the maximum temperature. As a result, the gas temperature again is shifted into the temperature range preferred for high equilibrium conversions.

Surprisingly, it was found that optimum methanol conversions, based on the respective reaction conditions, are obtained when the temperature of the reaction gas mixture in the conditioning zone asymptotically approaches the desired reactor outlet temperature. This is interpreted to the effect that in the presence of a sufficiently long flow path through the catalyst bed, the reaction gas mixture is given the opportunity to reach the equilibrium composition. By measuring axial temperature profiles in the catalyst bed in a manner known to the skilled person, it can be determined whether the asymptotic approach of the gas temperature to the reactor outlet temperature is effected under the given conditions. If this is not the case, the catalyst bed of the conditioning zone can be increased correspondingly. In principle, the more catalyst is required to reach the reaction equilibrium, the lower the desired maximum temperature in the catalyst bed.

Particularly preferably, the reactor according to the invention includes an adiabatic region as starting zone and a cooled region as moderator zone, wherein the moderator zone comprises means for cooling the feed stream by indirect heat exchange. In accordance with a particular aspect of the invention, the moderator zone optionally can also comprise one or more regions filled with catalyst.

In an advantageous configuration of the reactor according to the invention it is provided that the indirect heat exchange is effected in the moderator zone by a heat-transfer medium guided in cocurrent or countercurrent flow to the feed stream. Preferably, the unreacted, gaseous or vaporous or liquid feed stream is used as heat-transfer medium before being supplied to the reactor and is preheated at the same time, so that the demand of external energy for heating the feed stream is lowered before the same is charged to the reactor.

In principle, cooling can also be effected by evaporation of a liquid at a temperature which is slightly below the desired reaction gas temperature. For this purpose, synthetic oils can be used. Since the technical expenditure for this solution is quite considerable, however, this aspect of the invention is preferred less. Further useful cooling means include salt baths.

When heat exchangers are used, uncooled catalyst beds can additionally be employed before and/or after the cooled catalyst bed, i.e. before and/or after the heat exchanger. The uncooled bed before the heat exchanger serves as starting zone in which the reaction gas is heated, until a temperature is reached at which the reaction rate is high, but the formation of by-products is negligible. In the succeeding cooled catalyst bed(s) of the moderator zone, the reaction proceeds, but the reaction gas temperature is kept below the specified maximum temperature. The maximum temperature is fixed in consideration of rather high reaction rates (promoted by high temperatures), rather high equilibrium conversions (promoted by low temperatures) and a rather low formation of by-products (promoted by low temperatures) and can be determined by routine experiments or kinetic-thermodynamic optimization calculations.

In all embodiments of the reactor according to the invention, the feed stream must be superheated to a reactor inlet temperature which permits a kick-off of the dehydration reaction. Suitable temperatures are dependent on the gas composition and can be determined by routine experiments. In principle, the temperature window suitable for the methanol dehydration to DME is known from the prior art.

Particularly preferably, the reactor according to the invention also includes a conditioning zone, i.e. a last adiabatic region filled with catalyst, which is arranged before exit from the reactor, wherein in the conditioning zone a last part of the feed stream reacts exothermally to obtain DME and wherein the temperature of the feed stream is increased to a reactor outlet temperature. The flexibility of the reactor according to the invention is increased thereby, as in this way the gas temperature in the moderator zone can safely be kept below a defined maximum value by intensifying the heat exchange in a manner known to the skilled person, whereby the formation of by-products is minimized.

Yield losses of DME by lowering the reaction rate due to cooling below the desired reactor outlet temperature in the moderator zone are compensated by the subsequent post-reaction in the conditioning zone, with the reaction rate rising again due to the adiabatic heating of the gaseous reaction mixture. The downstream arrangement of such conditioning zone in particular is expedient when using a counterflow heat exchanger, as in this way an asymptotic approach of the reaction gas temperature to the desired reactor outlet temperature becomes possible.

When the heat exchanger is operated in cocurrent flow (reaction gas and cooling medium flow in the same direction), a high temperature difference between cooling medium and reaction gas is available at the entry of the reaction gas into the heat exchanger. As in this region of the heat exchanger a large amount of educt, i.e. methanol, also is reacted, a comparatively large amount of reaction heat is released, which can be dissipated. Cooling gas mass flow and temperature then are adjusted such that at the outlet from the heat exchanger the desired reaction gas outlet temperature is achieved. At the end of the heat exchanger only little reaction heat is released, and the temperature difference between reaction gas and cooling medium is relatively small. The reaction gas temperature asymptotically approaches the desired outlet temperature, which in this case is identical with the maximum temperature in the reactor. A final, uncooled catalyst bed as conditioning zone mostly is not expedient in this case.

When the heat exchanger is operated in countercurrent flow (reaction gas and cooling medium flow in opposite directions), only a small temperature difference between cooling gas and reaction gas is available at the entry of the reaction gas into the heat exchanger, because the cooling gas already has traversed the heat exchanger and has been heated. The heat exchange correspondingly is reduced. Therefore, the reaction gas temperature will continue to rise, until the thermal equilibrium between reaction heat released and heat discharged is reached. Mass flow and inlet temperature of the cooling medium are adjusted such that the fixed maximum temperature in the reaction gas is not exceeded. At the end of the cooled catalyst bed in the moderator zone, this can lead to a reaction gas temperature which lies below the desired reactor outlet temperature, depending on temperature level and catalyst bed length. The reaction rate thereby is reduced unnecessarily and the amount of catalyst required for approaching the reaction equilibrium is increased. In this case, it is expedient to reduce the size of the cooled catalyst bed in the moderator zone and to install an uncooled catalyst bed as conditioning zone behind the cooled catalyst bed.

In the uncooled catalyst bed of the conditioning zone, the reaction temperature rises only slowly, as only the residual methanol conversion takes place for approaching the reaction equilibrium. In this final, uncooled catalyst bed an asymptotic approach to the reaction equilibrium takes place at the desired reaction gas outlet temperature.

When using a tubular reactor in the moderator zone, the catalyst can be filled on the shell side or on the tube side. From a practical point of view, it mostly is preferred to fill the tube side with catalyst, in order to provide for an easier replacement of the catalyst.

In a further preferred configuration of the reactor according to the invention it is provided that the reactor has an adiabatic region according to claim 1, item (b), an adiabatic region according to claim 1, item (d), and optionally further adiabatic regions, wherein between two adjacent adiabatic regions each a cooled region (moderator zone) is present, wherein the moderator zones comprise means for cooling the feed stream by direct heat exchange. Advantageously, the direct heat exchange is effected by introducing a gaseous and/or liquid cooling medium which contains the feedstock methanol. In this way, a good cooling effect is obtained and at the same time evaporation energy for the feedstock methanol is saved. Alternatively, the maximum occurring temperature can be reduced by introducing reaction-neutral recycle gas as heat carrier. However, this is expensive, because the recycle gas must be compressed again, and therefore less preferred.

It was found to be particularly advantageous to design the reactor such that the same comprises at least three adiabatic regions and at least two regions cooled by means of direct heat exchange, wherein between two adjacent adiabatic regions each a cooled region (moderator zone) is arranged. In a configuration of the reactor with three adiabatic regions and two cooling zones with direct heat exchange arranged between the same, an apparatus is obtained which is easily manageable in terms of temperature control, but constructively simple. There is adjusted a high methanol conversion in the first stages of the reactor and a lower residual conversion in the last stage of the reactor. Via the temperature and the mass flow of the cooling medium introduced for example by injection or spraying in, the desired temperature profile is adjusted. In the last catalyst bed an asymptotic approach to the reaction equilibrium takes place at the desired reaction gas outlet temperature.

Further developments, advantages and possible applications of the invention can also be taken from the following description of exemplary embodiments and numerical examples and the drawings. All features described and/or illustrated form the invention per se or in any combination, independent of their inclusion in the claims or their back-reference.

For a better understanding of the mode of operation of the reactors according to the invention, the typical temperature profiles each obtained also are illustrated in the drawings. There are shown the respective temperature increases $T-T_i$ with the reactor inlet temperature $T_i$ as reference point in dependence on the reactor length coordinate x. Suitable reactor inlet temperatures lie in the temperature range between 200 and 300° C. and can be determined by routine experiments. $T_o$ designates the reactor outlet temperature.

In the adiabatic fixed-bed reactor 101 according to the prior art, which is schematically shown in FIG. 1, the vaporous feed stream 102 containing methanol enters into the reactor and the catalyst bed 103 after evaporation and superheating, which catalyst bed consists of a DME dehydration catalyst on the basis of γ-alumina of Süd-Chemie AG, Munich. In the present example, the space velocity of the feed stream is 2 kg/(kg h), the pressure at the reactor inlet is about 16 bar. The fixed-bed reactor used is thermally insulated on the outside, in order to avoid heat losses. Due to the exothermal reaction of the methanol in the feed stream the gas temperature rises by about 115° C., while the feed stream passes through the fixed-bed reactor. Due to the missing heat dissipation via the reactor wall, this maximum temperature corresponds to the reactor outlet temperature. In the present example, the ratio between catalyst volume and space velocity is chosen such that the equilibrium conditions are reached already distinctly before leaving the reactor, as shown with reference to the asymptotic approach of the axial temperature profile shown in the upper region of FIG. 1 to the maximum temperature. (Case (A)). The reacted gas stream leaves the fixed-bed reactor as exit stream 104.

Figure 2:
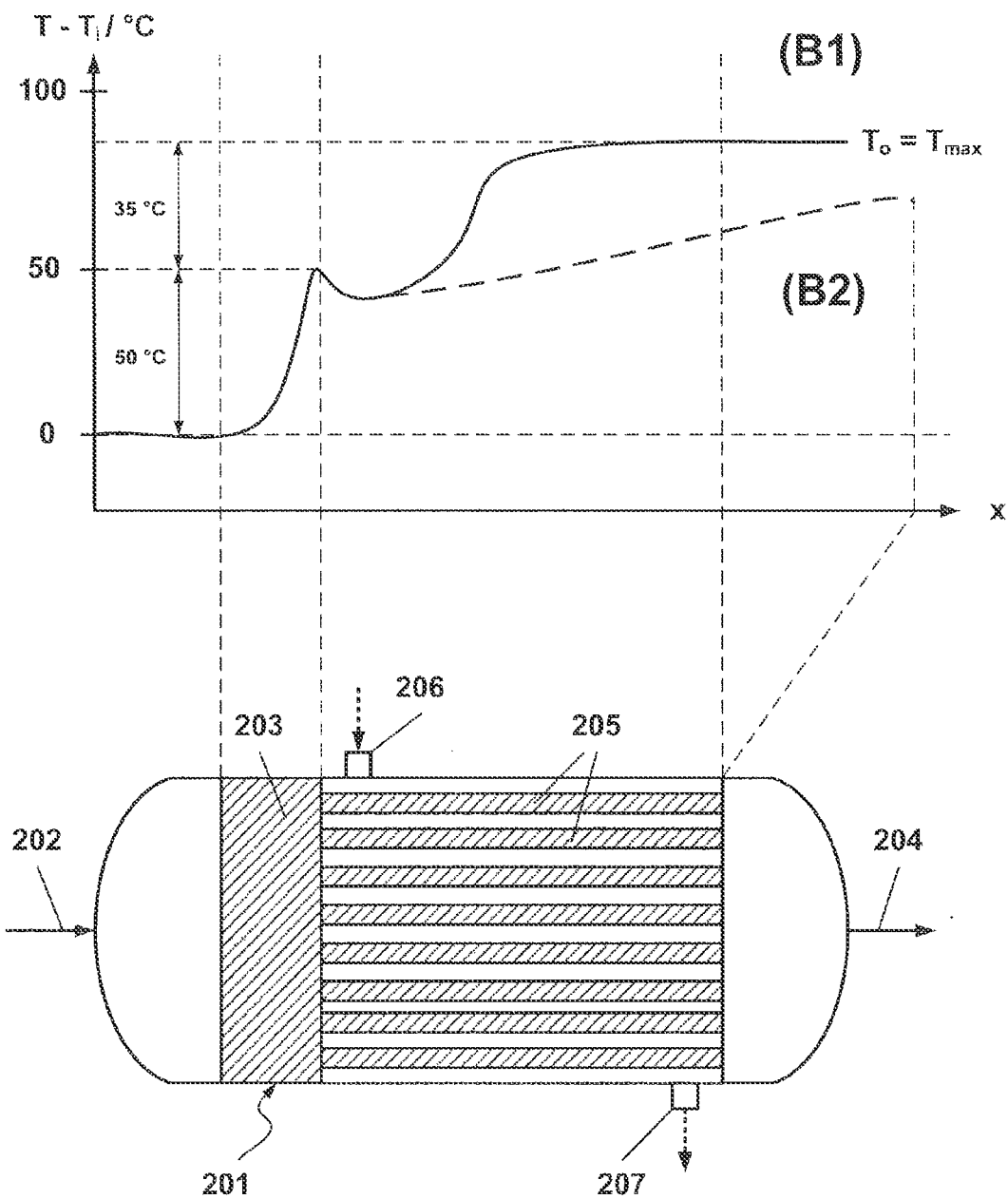
FIG. 2 schematically shows a reactor according to the invention in a first embodiment.

In the fixed-bed reactor 201 according to a first aspect of the invention, which is schematically shown in FIG. 2, the feed stream 202 enters into the reactor and the adiabatic catalyst bed 203, which forms the starting zone of the reactor. In the present case, the catalyst volume in the starting zone is about 25% of the catalyst volume of the comparative example shown in FIG. 1, but there is used the same type of catalyst. The percentage of the starting zone in the catalyst volume is greatly dependent on the configuration of the heat exchanger and the resulting temperature profile in the cooled catalyst bed. The residual catalyst volume is arranged in the succeeding moderator zone 205, which is designed as cocurrent tubular heat exchanger. In the exemplary embodiment of FIG. 2, there is no conditioning zone. In the case B1, the total catalyst volume installed corresponds to the one from the comparative example, so that the space velocity related to the total catalyst volume also is the same. The reactor pressure corresponds to that from the comparative example. The catalyst in the moderator zone is located in the heat exchanger tubes, whereas the shell side of the heat exchanger is traversed by vaporous methanol as cooling medium, which enters into the heat exchanger through the coolant inlet 206 and leaves the heat exchanger through the coolant outlet 207.

When the feed stream passes through the starting zone, it is again adiabatically heated by the exothermal reaction of the methanol. Due to the limited catalyst volume in the starting zone, only a part of the methanol contained therein is reacted. After leaving the starting zone and entering into the moderator zone, a noticeable slow-down of the temperature increase initially occurs in the present example or even, as shown in the associated axial temperature profile in FIG. 2, a little cooling of the reaction gas stream, as due to the cocurrent operation of the heat exchanger the reaction gas stream meets with cold cooling medium at the entry into the moderator zone. Due to the further reaction of the methanol during the further passage of the reaction gas stream through the moderator zone, heating occurs again, which however proceeds less steeply than in the comparative example of FIG. 1. This results in a lower increase in temperature as compared to the purely adiabatic case (A) of FIG. 1. As compared to the adiabatic case (A), higher methanol equilibrium conversions therefore are to be expected. In the temperature profiles shown in FIG. 2, a distinction is made between an asymptotic case (B1) (continuous curve) and a non-asymptotic case (B2) (broken curve). In the latter case, no equilibrium conditions do yet exist upon exit of the reaction gas stream from the moderator zone. This can be overcome by increasing the catalyst volume in the moderator zone. The two curves differ in the desired maximum reaction gas temperature. The reacted gas stream leaves the fixed-bed reactor as exit stream 204. In the case B1, the increase in temperature is about 85° C., and in the case B2 with increased catalyst bed about 55° C.

Figure 3:
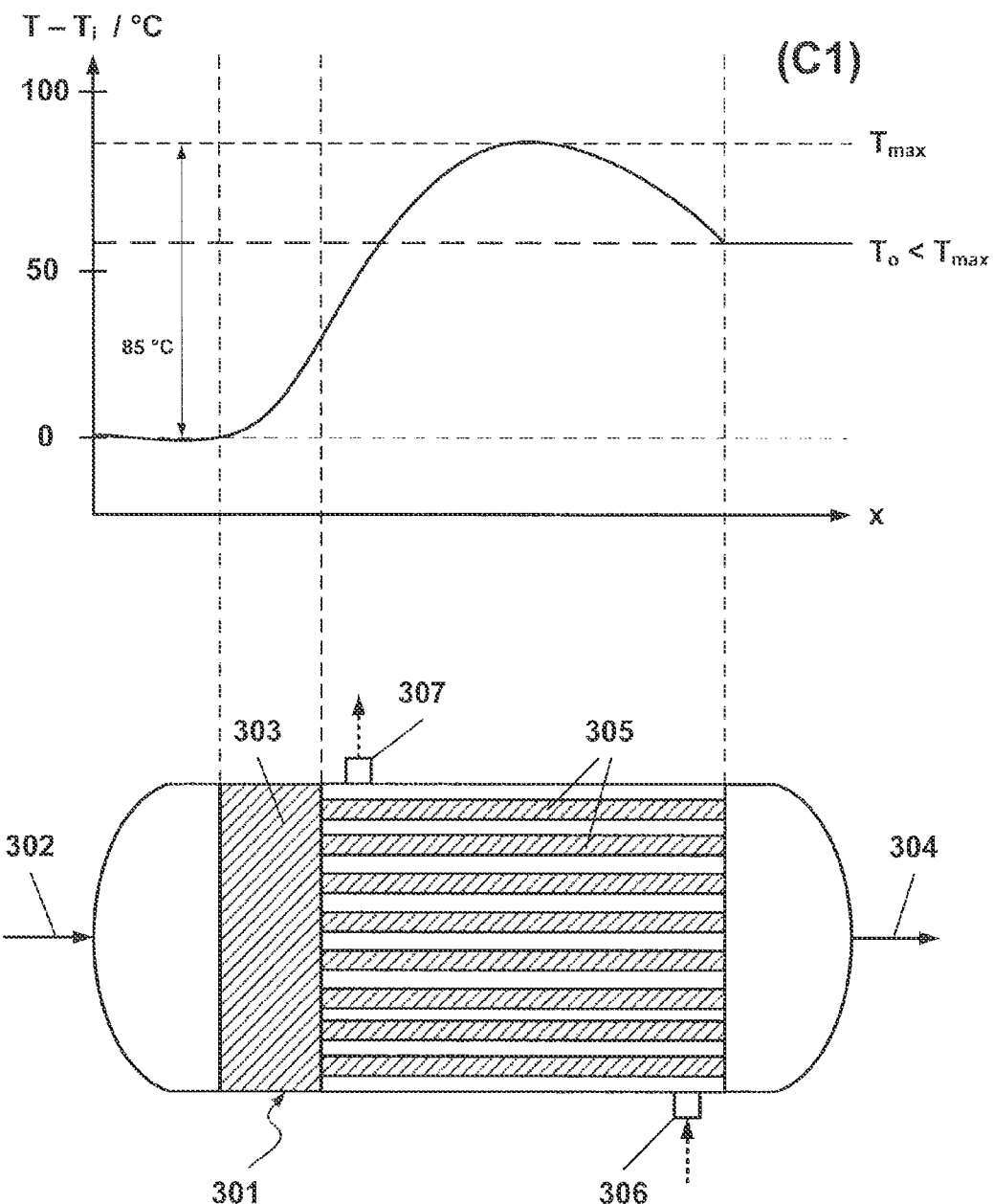
FIG. 3 schematically shows a reactor according to the invention in a second embodiment.

A difference of the fixed-bed reactor 301 according to a second aspect of the invention, which is schematically shown in FIG. 3, to the previously discussed exemplary embodiment of FIG. 3 merely consists in the reversal of the flow direction of the cooling medium through the moderator zone 305; all other conditions correspond to those of the exemplary embodiment of FIG. 2.

Since the heat exchanger of the moderator zone now is operated as counterflow heat exchanger, the cooling of the reaction gas stream entering into the moderator zone is less strong than in the exemplary embodiment of FIG. 2. By the choice of the inlet temperature and the volume flow of the cooling medium through the heat exchanger it is, however, dimensioned such that a fixed maximum temperature is not exceeded. In the present example, the maximum temperature lies 85° C. above the reactor inlet temperature. This is important for suppressing the formation of undesired by-products, whose reactions of formation mostly proceed irreversibly. After passing through the maximum temperature, the reaction gas stream cools down more and more, since less and less methanol reacts exothermally to obtain DME, but at the same time the dissipated heat quantities remain relatively constant due to the characteristic of the counterflow heat exchanger. In the present example, the reacted gas stream leaves the reactor as exit stream 304 with a reactor outlet temperature which lies about 55° C. above the reactor inlet temperature. The axial temperature profile shown in FIG. 3 corresponds to a non-asymptotic case (C1). Accordingly, no equilibrium conditions do yet exist upon exit of the reaction gas stream from the moderator zone.

Figure 4:
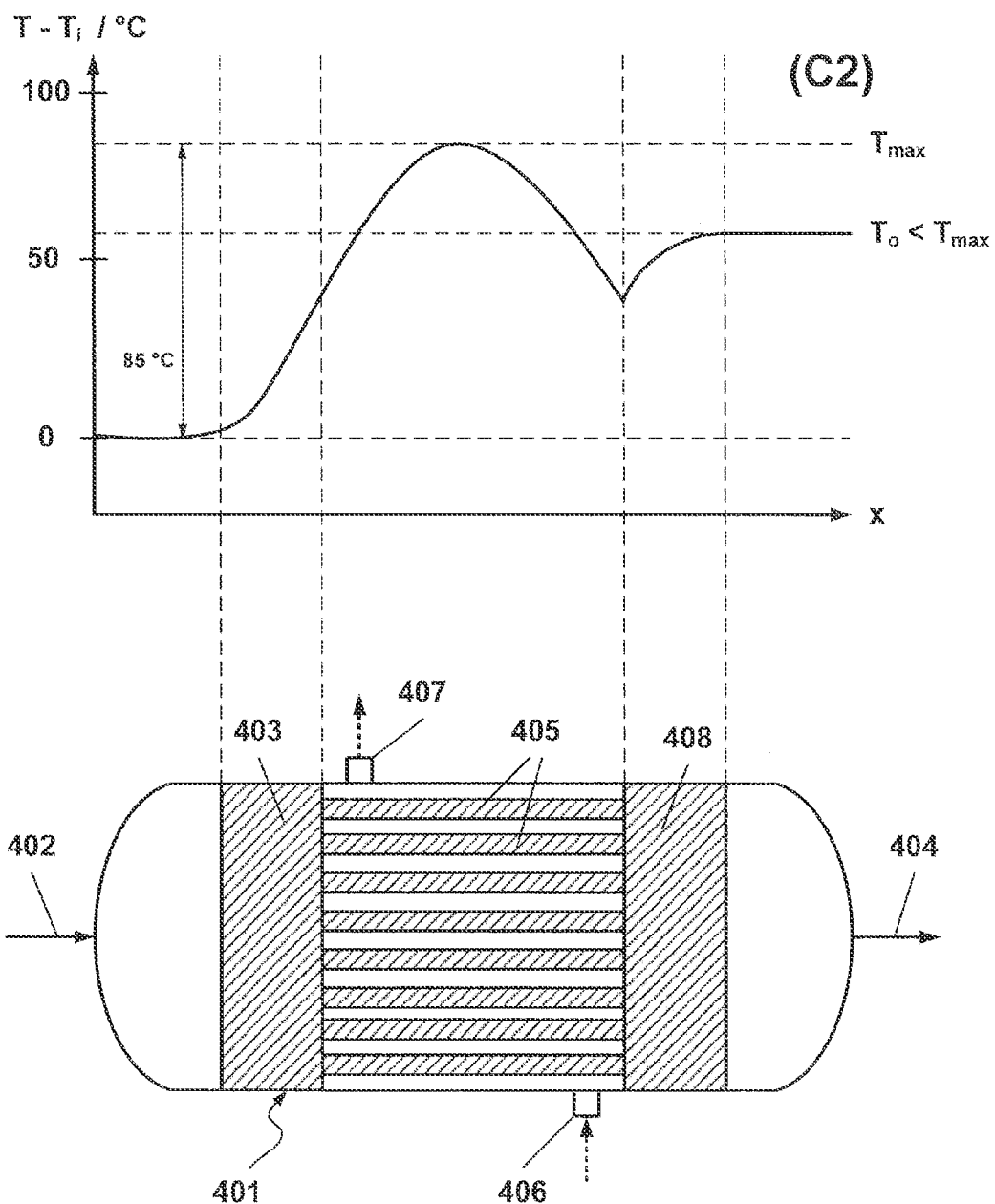
FIG. 4 schematically shows a reactor according to the invention in a third embodiment.

In the fixed-bed reactor 401 schematically shown in FIG. 4 the catalyst bed is divided into a starting zone 403 (about 20% of the catalyst volume, adiabatic fixed bed), a moderator zone 405 (about 30% of the catalyst volume, counterflow tubular heat exchanger) and a final conditioning zone 408 (about 50% of the catalyst volume, adiabatic fixed bed). All other conditions correspond to those of the exemplary embodiment of FIG. 3. As compared to the reactor without conditioning zone, which is shown in FIG. 3, the reactor 401 offers greater flexibility with regard to the choice of the maximum temperature and thus the suppression of undesired side reactions. In the present example, the maximum temperature again lies 85° C. above the reactor inlet temperature. As before entry of the reaction gas stream into the conditioning zone, large parts of the methanol have already been reacted, the conditioning zone substantially serves the adjustment of the reaction equilibrium at the reactor outlet temperature. In the present example, it lies about 50° C. above the reactor inlet temperature.

Figure 5:
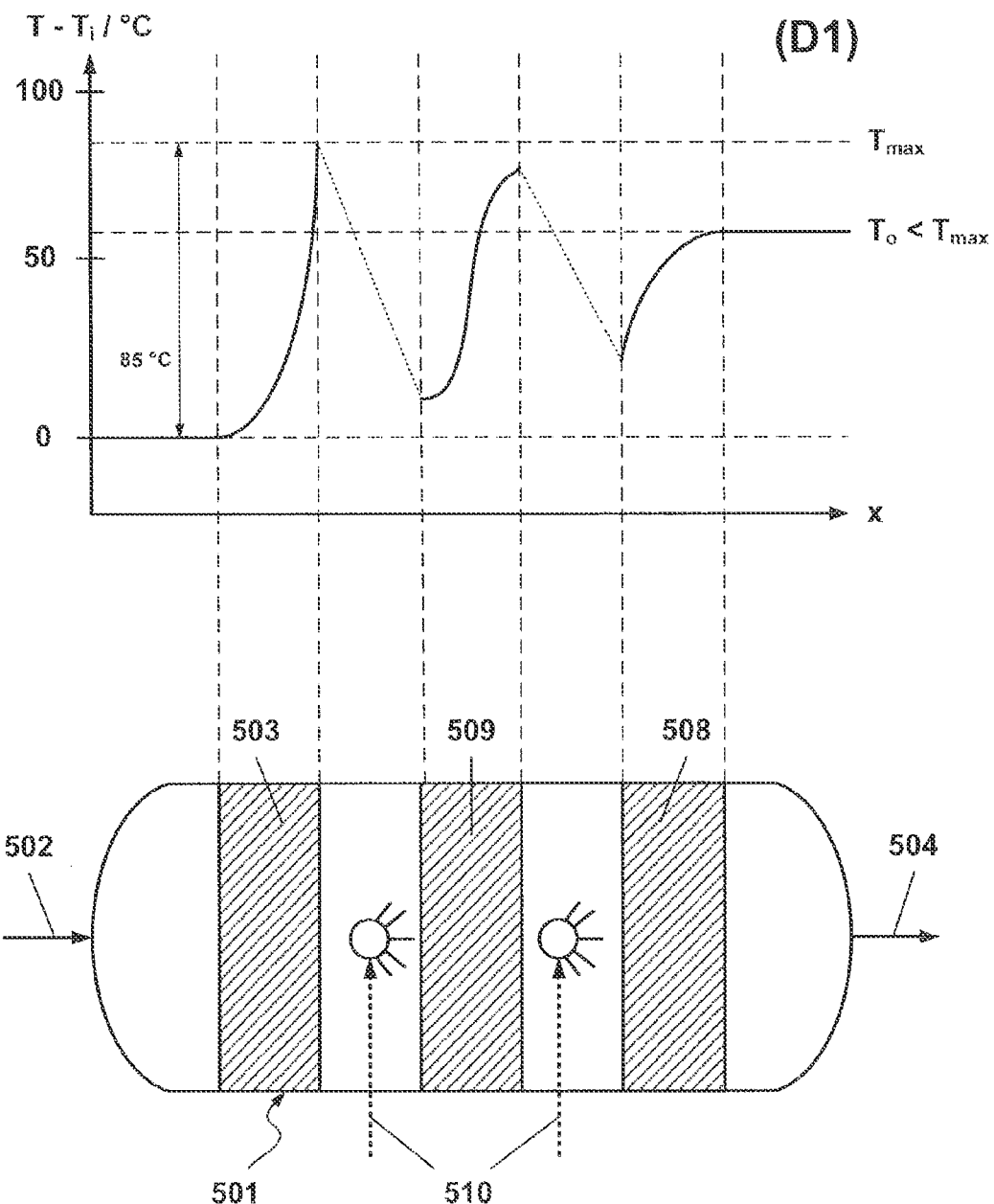
FIG. 5 schematically shows a reactor according to the invention in a fourth embodiment.

FIG. 5 schematically shows a configuration of the reactor according to the invention, in which instead of the indirect heat exchange the direct heat exchange is employed by introducing a cooling medium into the moderator zones. In the present example, three adiabatic catalyst beds are present, wherein the catalyst bed arranged on the inlet side serves as starting zone 503 and the catalyst bed arranged on the outlet side serves as conditioning zone 508. Between the same, a further adiabatic catalyst bed 509 is arranged. The total catalyst quantity present in the three catalyst beds and the type of catalyst correspond to those in the exemplary embodiment discussed in FIG. 4 (case C2). In the present example, the space velocity of the feed stream related to the total catalyst volume installed again is 2 kg/(kg h). The pressure at the reactor inlet corresponds to the one from the comparative example. Between the first catalyst bed 503 and the second catalyst bed 509 as well as between the second catalyst bed 509 and the third catalyst bed 508 a free space each is present as moderator zone, in which one device 510 each is arranged for injecting liquid methanol as cooling medium. The same substantially consist of a conical nozzle, feed conduits and flow controllers. With larger reactor diameters it is expedient to connect several conical nozzles in parallel, in order to uniformly distribute the cooling medium over the reactor cross-section. Based on the methanol quantity present in the feed stream 502, the methanol quantity injected is about 10 to 20%.

The feed stream 502 enters into the reactor 501. When the feed stream passes through the adiabatic catalyst bed 503 of the starting zone, the same is heated up by about 85° C., which at the same time corresponds to the maximum temperature. The reaction gas stream then enters into the first moderator zone and is cooled by injecting liquid methanol. The required temperature is higher than the reactor inlet temperature and is chosen such that in the following bed the maximum temperature is not exceeded. The mixing and temperature compensation processes in the moderator zone are complex; in the temperature profile of FIG. 5 cooling is indicated only schematically and in simplified form. After leaving the first moderator zone, the reaction gas stream enters into the second adiabatic catalyst bed 509. In this bed, the further reaction takes place, wherein in the second adiabatic catalyst bed less methanol is converted and thus the heat quantity released is smaller than in the first adiabatic catalyst bed. After flowing through the second adiabatic catalyst bed, the reaction gas enters into the second moderator zone. In this zone, liquid methanol in turn is injected for cooling the reaction gas stream to a temperature which is required to achieve an equilibrium conversion without exceeding the desired outlet temperature in the succeeding conditioning zone 508. Since again less methanol is converted in the conditioning zone, the temperature increase is reduced as compared to the preceding catalyst beds. To avoid too much cooling of the reaction gas stream and thus too small reaction rates, it is expedient to choose the amount of cooling medium introduced into the second moderator zone smaller than the amount of cooling medium introduced into the first moderator zone. Alternatively, the cooling medium introduced into the second moderator zone can be preheated to a temperature above the ambient temperature. This allows to choose the amount of cooling medium introduced into the second moderator zone even larger than the amount of cooling medium introduced into the first moderator zone.

After leaving the second moderator zone, the reaction gas stream enters into the final catalyst fixed bed 508 serving as conditioning zone. As before entry of the reaction gas stream into the conditioning zone, large parts of the methanol have already been reacted, the conditioning zone substantially serves the adjustment of the reaction equilibrium at the reactor outlet temperature. As a result, there is again obtained a course of the axial temperature profile which asymptotically approaches the outlet temperature. The reaction gas stream finally leaves the reactor 501 as exit stream 504 with a reactor outlet temperature which lies about 50° C. above the reactor inlet temperature.

The conversion and temperature behavior of the configurations of the reactor according to the invention as shown in FIG. 2 to FIG. 5 was calculated with a calculation model based on experimentally obtained measured values and compared with the adiabatic fixed-bed reactor shown in FIG.

1 as comparative example. The tolerable maximum temperatures were set between 85° C. and 55° C. above the reactor inlet temperature. The indicated values were achieved with a one-time passage through the reactor, i.e. without taking account of a recirculation of the non-converted methanol. The feed gas was pure methanol. The space velocity was the same in all cases and amounted to 2 kg/(kg h). The results of the calculations are listed in Tables 1 to 3.

TABLE 1

Comparison of the adiabatic, uncooled reactor with the reactor cooled by a cocurrent heat exchanger

| Exemplary embodiment | FIG. 1, Case A (Comp. Ex.) | FIG. 2, Case B1 (Invention) | FIG. 2, Case B2 (Invention) |
|---|---|---|---|
| Type of reactor | Uncooled adiabatic reactor | Cooling by heat exchanger in cocurrent flow | Cooling by heat exchanger in cocurrent flow |
| Relative installed catalyst quantity/% | 100 | 100 | 120 |
| Relative quantity of non-converted methanol/% | 100 | 93 | 88 |
| Relative quantity of by-products formed ($CO$, $CO_2$, $H_2$, $CH_4$)/% | 100 | 16 | 5 |

TABLE 2

Comparison of the adiabatic, uncooled reactor with the reactor cooled by a countercurrent heat exchanger

| Exemplary embodiment | FIG. 1, Case A (Comp. Ex.) | FIG. 3, Case C1 (Invention) | FIG. 4, Case C2 (Invention) | Case C3 (Invention) |
|---|---|---|---|---|
| Type of reactor | Uncooled adiabatic reactor | Cooling by heat exchanger in countercurrent flow | Cooling by heat exchanger in countercurrent flow | Cooling by heat exchanger in countercurrent flow |
| Relative installed catalyst quantity/% | 100 | 100 | 100 | 120 |
| Relative quantity of non-converted methanol/% | 100 | 88 | 85 | 87 |
| Relative quantity of by-products formed ($CO$, $CO_2$, $H_2$, $CH_4$)/% | 100 | 16 | 16 | 5 |

TABLE 3

Comparison of the adiabatic, uncooled reactor with the reactor cooled by introducing a cooling medium

| Exemplary embodiment | FIG. 1, Case A (Comp. Ex.) | FIG. 5, Case D1 (Invention) | Case D2 (Invention) | Case D3 (Invention) |
|---|---|---|---|---|
| Type of reactor | Uncooled adiabatic reactor | Cooling by cooling medium (3-stage) | Cooling by cooling medium (3-stage) | Cooling by cooling medium (3-stage) |
| Relative installed catalyst quantity/% | 100 | 100 | 120 | 120 |
| Relative quantity of non-converted methanol/% | 100 | 90 | 86 | 90 |
| Relative quantity of by-products formed ($CO$, $CO_2$, $H_2$, $CH_4$)/% | 100 | 16 | 16 | 5 |

In Table 1, the conversion and temperature behavior of the adiabatic, uncooled fixed-bed reactor is compared with that of the reactor cooled by a cocurrent heat exchanger according to the embodiment shown in FIG. 2, which is equipped with an adiabatic starting zone (case B1). It can be seen that with the same catalyst quantity installed and a reduction of the maximum temperature in the reactor to 85° C. above the reactor inlet temperature, the non-converted methanol quantity is reduced, since the equilibrium conversion increases with decreasing temperature. At the same time, the amount of by-products formed is distinctly decreased by reduction of the maximum temperature in the reactor.

With a reduction of the maximum temperature to 55° C. above the reactor inlet temperature, about 20% more of catalyst is required because of the distinctly reduced reaction rate, in order to achieve an approach to the reaction equilibrium. This corresponds to the case B2 represented as broken curve in FIG. 2. What can again be seen is the asymptotic approach of the temperature profile to the outlet temperature and to the reaction equilibrium belonging to this outlet temperature, respectively. The amount of non-converted methanol and of by-products formed again is reduced as compared to the case B1.

In Table 2, the conversion and temperature behavior of the adiabatic, uncooled fixed-bed reactor is compared with that of the reactor cooled by the countercurrent heat exchanger according to the embodiment shown in FIG. 3 (case C1) and the embodiment shown in FIG. 4 (case C2). In case C1, only an adiabatic starting zone is present, whereas the case C2 includes an adiabatic starting zone and an adiabatic conditioning zone. Case C3 corresponds to the configuration of case C2, but here the admissible maximum temperature of the reaction gas was reduced, which increases the catalyst quantity required for approaching the reaction equilibrium. With equal reactor inlet temperature, equal reactor outlet temperature and equal catalyst volume, a lower amount of non-converted methanol surprisingly was observed in case C2 as compared to case C1. This becomes possible by providing the adiabatic conditioning zone, in which the reaction gas temperature asymptotically approaches the desired reactor outlet temperature. Analogous to the results shown in Table 1, the amount of by-products formed also is reduced in a configuration of the reactor according to the invention with a moderator zone cooled by a countercurrent heat exchanger, in that the maximum temperature in the reactor is reduced.

In Example C3, the maximum temperature of the reaction gas was limited to 65° C. above the reactor inlet temperature. Due to the reaction rate reduced thereby, the equilibrium conversion is not yet reached completely even with a catalyst feedstock increased by 20%.

In Table 3, the conversion and temperature behavior of the adiabatic, uncooled fixed-bed reactor is compared with the configuration of the reactor according to the invention, in which cooling is effected by introducing a cooling medium between the adiabatic catalyst beds (FIG. 5, case D1). Here, the case with three adiabatic catalyst beds and coolant injections between the first and second catalyst bed as well as between the second and third catalyst bed was calculated, with liquid methanol being injected as cooling medium. Here as well, by reducing the maximum temperature in the reactor, the amount of non-converted methanol and the amount of by-products formed can be reduced (FIG. 5, case D1). A further decrease of the amount of non-converted methanol can be achieved by increasing the installed catalyst volume (case D2, not shown in FIG. 5). For a further decrease of the amount of by-products formed, it is necessary, however, to decrease the maximum temperature to 65° C. above the reactor inlet temperature. To avoid that this is effected at the expense of a rise in the amount of non-converted methanol, an increase of the installed catalyst volume is necessary at the same time (case D3, not shown in FIG. 5).

In long-term operation, the activity of the catalyst will decrease according to experience. This can be compensated by an additionally installed catalyst mass or by raising the operating temperature. When high operating temperatures are achieved at the beginning of the operation with unused catalyst, like in the uncooled reactor, the loss of activity can only be compensated by an additionally installed catalyst. The lower the chosen maximum operating temperatures, the less catalyst must additionally be installed for the long-term operation, since a possible loss of activity of the catalyst can wholly or partly be compensated by raising the operating temperature. Higher operating temperatures towards the end of the catalyst life, however, will lead to a reduction of the methanol conversion and the selectivity to DME.

Industrial Applicability

The present invention provides an optimized reactor for the catalytic dehydration of methanol to dimethyl ether in different configurations. By increasing the methanol conversion in the reactor according to the invention, the cycle streams of non-converted methanol in a commercial plant are lowered, which contributes to an improved economy of the process. By avoiding the formation of by-products, the purity of the DME product obtained is increased and the expenditure required for purifying the product is reduced.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B, and C" should be interpreted as one or more of a group of elements consisting of A, B, and C, and should not be interpreted as requiring at least one of each of the listed elements A, B, and C, regardless of whether A, B, and C are related as categories or otherwise. Moreover, the recitation of "A, B, and/or C" or "at least one of A, B, or C" should be interpreted as including any singular entity from the listed elements, e.g., A, any subset from the listed elements, e.g., A and B, or the entire list of elements A, B, and C.

List of Reference Numerals

[101], [201], [301], [401], [501] reactor
[102], [202], [302], [402], [502] reactor inlet
[103], [203], [303], [403], [503] adiabatic catalyst bed, starting zone
[104], [204], [304], [404], [504] reactor outlet
[105], [205], [305], [405] moderator zone
[206], [306], [406] entry cooling medium
[207], [307], [407] exit cooling medium
[408], [508] conditioning zone
[509] adiabatic catalyst bed
[510] injection cooling medium

The invention claimed is:
1. A reactor, comprising:
a starting zone;
an adiabatic region;
a cooled region;
a fixed bed zone; and
a moderator zone,
wherein the reactor is configured to produce dimethyl ether (DME) by heterogeneously catalyzed dehydration of a gaseous feed stream comprising methanol,
wherein the dehydration occurs over a solid catalyst suitable to dehydrate methanol to DME under dehydration conditions,
wherein the reactor is configured such that a temperature of the gaseous feed stream approaches a desired reactor outlet temperature asymptotically,
(a) wherein the reactor is configured such that, in the starting zone, after entry into the reactor, the gaseous feed stream initially flows through the adiabatic region, comprising the catalyst, and a first part of the methanol exothermally reacts to provide DME under methanol dehydration conditions,
wherein, in the starting zone, a feed stream temperature is increased with respect to a reactor inlet temperature, and the feed stream temperature does not exceed a target maximum temperature,
(b) wherein the reactor is configured such that, in the moderator zone, the gaseous feed stream subsequently passes through at least one cooled region, wherein, in the moderator zone, reaction heat released is at least partly dissipated and a feed stream temperature increase is at least reduced, and (c) wherein the reactor is optionally configured such that, in a conditioning zone, before the gaseous feed stream exits the reactor, the gaseous feed stream flows through a last adiabatic region, comprising the catalyst, and a second part of the methanol comprised in the feed stream exothermally reacts to provide DME under methanol dehydration conditions, and the feed stream temperature is increased to a reactor outlet temperature.

2. The reactor of claim 1, wherein the moderator zone comprises
a region comprising the catalyst, and
a unit configured to cool the feed stream by indirect heat exchange.

3. The reactor of claim 2, wherein the indirect heat exchange is effected by a heat-transfer medium guided in flow to the feed stream.

4. The reactor of claim 3, wherein the heat-transfer medium comprises unreacted feed stream comprising methanol before the unreacted feed stream is supplied to the reactor.

5. The reactor of claim 1, comprising:
the conditioning zone.

6. The reactor of claim 1, arranged as a series, optionally repeated, including:
the starting zone including the adiabatic region;
the conditioning zone including a further adiabatic region; and
the moderator zone including the cooled region between each two respective adjacent adiabatic regions,
wherein each moderator zone comprises a unit configured to cool the feed stream by direct heat exchange.

7. The reactor of claim 6, wherein the direct heat exchange is effected by introducing a gaseous, liquid, or gaseous and liquid cooling medium.

8. The reactor of claim 7, wherein the cooling medium comprises methanol.

9. The reactor of claim 6, comprising at least three adiabatic regions and at least two cooled regions, wherein one of the at least two cooled regions is arranged between each two respective adjacent adiabatic regions.

10. A process for producing dimethyl ether (DME), the process comprising:
(a) dehydrating, by heterogeneous catalysis, a gaseous feed stream comprising methanol over a solid catalyst suitable to dehydrate methanol to DME, under methanol dehydration conditions in the reactor of claim 1, to obtain a product stream comprising DME;
(b) recovering DME from the product stream.

11. The reactor of claim 5, further comprising, after the conditioning zone:
an additional adiabatic region comprising the catalyst, an additional cooled region, or two or more of any of these, through which the feed stream passes.

12. The reactor of claim 1, configured such that, in the moderator zone, the feed stream temperature increase is reversed.

13. The reactor of claim 2, wherein the indirect heat exchange is effected by a heat-transfer medium guided in countercurrent flow to the feed stream.

14. The reactor of claim 4, wherein the unreacted feed stream comprises liquid methanol.

15. The reactor of claim 4, wherein the unreacted feed stream comprises gaseous methanol.

16. The reactor of claim 14, wherein the unreacted feed stream comprises gaseous methanol.

17. The reactor of claim 1, wherein the moderator zone includes a tubular reactor region.

18. The reactor of claim 1, configured such that the temperature of the gaseous feed stream in the conditioning zone approaches the desired reactor outlet temperature asymptotically.

19. The reactor of claim 9, wherein each cooled zone is in contact with a tubular moderator zone.

20. The reactor of claim 1, wherein the conditioning zone is present and comprises at least 50 vol. % of the catalyst.

* * * * *